United States Patent
Rivelli, Jr.

(10) Patent No.: US 6,899,730 B1
(45) Date of Patent: May 31, 2005

(54) CATHETER-STENT DEVICE

(75) Inventor: Patrick Rivelli, Jr., Palo Alto, CA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/548,682

(22) Filed: Apr. 13, 2000

Related U.S. Application Data

(60) Provisional application No. 60/129,672, filed on Apr. 15, 1999, and provisional application No. 60/129,668, filed on Apr. 15, 1999.

(51) Int. Cl.$^7$ .................................................. A61F 2/06
(52) U.S. Cl. ...................................... 623/1.15; 623/1.11
(58) Field of Search ....................... 623/1.11, 1.15–1.22, 623/1.1, 1.2, 12, 1.12, 1.13, 1.21, 1.3, 1.33, 1.54; 606/191, 194, 198

(56) References Cited

U.S. PATENT DOCUMENTS

| | | | |
|---|---|---|---|
| 4,503,569 A | 3/1985 | Dotter ........................ 623/1.19 |
| 4,505,767 A | 3/1985 | Quin ........................... 148/402 |
| 4,512,338 A | 4/1985 | Balko et al. ................. 606/108 |
| 4,553,545 A | 11/1985 | Maass et al. ................ 606/198 |
| 4,665,918 A * | 5/1987 | Garza et al. ................. 606/108 |
| 4,760,849 A * | 8/1988 | Kropf .......................... 606/191 |
| 4,795,485 A | 1/1989 | Pasteris ....................... 504/213 |
| 4,820,298 A | 4/1989 | Leveen et al. .............. 623/1.18 |
| 4,830,003 A * | 5/1989 | Wolff et al. ................. 606/198 |
| 5,067,957 A | 11/1991 | Jervis .......................... 606/108 |
| 5,108,417 A * | 4/1992 | Sawyer ....................... 606/198 |
| 5,217,484 A | 6/1993 | Marks ......................... 606/200 |
| 5,342,387 A * | 8/1994 | Summers .................... 606/198 |
| 5,484,444 A * | 1/1996 | Braunschweiler et al. .. 606/108 |
| 5,540,712 A | 7/1996 | Kleshinski et al. ......... 606/198 |
| 5,551,954 A | 9/1996 | Buscemi et al. ............ 623/1.15 |
| 5,562,641 A | 10/1996 | Flomenblit et al. ......... 604/531 |
| 5,782,907 A | 7/1998 | Frantzen et al. ............. 623/1 |
| 5,824,053 A | 10/1998 | Khosravi .................... 623/1.22 |
| 5,833,694 A | 11/1998 | Poncet ........................ 606/108 |
| 5,836,966 A | 11/1998 | St. Germain ................ 606/198 |
| 5,860,999 A | 1/1999 | Schnepp-Pesch et al. ... 606/194 |
| 5,902,317 A | 5/1999 | Kleshinski et al. ......... 606/198 |
| 5,928,217 A * | 7/1999 | Mikus et al. ................ 604/530 |
| 5,938,697 A * | 8/1999 | Killion et al. ............... 623/12 |
| 6,019,779 A * | 2/2000 | Thorud et al. .............. 606/198 |
| 6,027,526 A * | 2/2000 | Limon et al. ................ 606/194 |
| 6,048,360 A | 4/2000 | Khosravi et al. ............. 623/1 |
| 6,123,723 A | 9/2000 | Konya et al. ................ 623/1.11 |
| 6,129,755 A | 10/2000 | Mathis et al. ............... 623/1.15 |
| 6,156,062 A | 12/2000 | McGuinness ............... 623/1.11 |
| 6,190,406 B1 | 2/2001 | Duerig et al. ................ 623/1.2 |
| 6,200,335 B1 * | 3/2001 | Igaki ........................... 623/1.15 |
| 6,261,320 B1 | 7/2001 | Tam et al. ................... 623/1.15 |
| 6,290,731 B1 | 9/2001 | Solovay et al. ............. 623/51.16 |
| 6,413,272 B1 | 7/2002 | Igaki ........................... 623/1.15 |
| 6,413,282 B1 | 7/2002 | Igaki et al. .................. 623/1.15 |
| 6,425,915 B1 * | 7/2002 | Khosravi et al. ............ 623/1.11 |

FOREIGN PATENT DOCUMENTS

| | | |
|---|---|---|
| WO | WO 93/15661 | 8/1993 |
| WO | WO 00/62711 | 10/2000 |

* cited by examiner

*Primary Examiner*—(Jackie) Tan-Uyen T. Ho
(74) *Attorney, Agent, or Firm*—Vidas,Arrett&Steinkraus PA

(57) ABSTRACT

A graftless prosthetic stent for treatment of vascular lesions such as aneurysms and arterio-venous fistulas, especially in neurovascular vessels, comprises a continuous helical ribbon formed of a shape-retaining metal having a transition temperature at which the stent expands from its contracted condition to a radially expanded condition, the stent remaining substantially cylindrical in its contracted and expanded conditions. The helical windings have variable width, thickness, number or size of openings, or combinations of these features, which affect the stiffness, rate of expansion at the transition temperature, and the area of vessel wall covered by the stent. A catheter device which includes the stent, and a method of treatment using the stent are also provided.

21 Claims, 20 Drawing Sheets

CATHETER-STENT DEVICE

The present application is related to U.S. provisional patent application Ser. No. 60/129,672, filed Apr. 15, 1999, and Ser. No. 60/129,668, filed Apr. 15, 1999, and incorporates both applications herein by reference.

FIELD OF THE INVENTION

The present invention relates to a vascular endoprosthesis, such as a stent, for placement in an area of a body lumen that has been weakened by damage or disease such as by aneurysm, and in particular, to a stent adapted for placement at a neurovascular site.

BACKGROUND OF THE INVENTION

Rupture of non-occlusive cerebrovascular lesions, such as intracranial saccular aneurysms or arterio-venous fistulae, are a major cause of stroke. Rupture of an aneurysm causes subarachnoid hemorrhage in which blood from a ruptured vessel spreads over the surface of the brain. About 2.5% of the United States population (4 million Americans) have an unruptured aneurysm. About 100,000 of these people suffer a subarachnoid hemorrhage. The disease is devastating, often affecting healthy people in their 40's and 50's, with about half of the rupture victims succumbing within a month, and with half of the survivors becoming seriously disabled as a result of the initial hemorrhage or of a delayed complication.

Neurovascular arteries are generally quite small, having diameters ranging from 2.0 to 4.0 mm in the Circle of Willis, 2.5 to 4.5 mm in the cavernous segment of the internal carotid artery, 1.5 to 3.0 mm in vessels of the distal anterior circulation, and 2.0 to 4.0 mm in the posterior circulation. The incidence of aneurysm varies with the location, with 55% occurring in the Circle of Willis, 30% in the internal carotid, 10% in the distal anterior circulation, and 5% in the posterior circulation.

Screening for these lesions and preventing rupture will lead to better clinical outcomes and lower costs. Non-invasive treatments for ruptured and unruptured lesions are preferred over surgical interventions due to lower costs, lower mortality and morbidity, and patient preference. An attractive treatment for ruptured and unruptured aneurysms is the placement of a stent within the lumen to prevent rupture or re-rupture of the lesion.

Stents formed of a helical coil or ribbon of shape-memory alloy material are known in the art. In general, such stents are formed to a desired expanded shape and size for vascular use above the transition temperature of the material. The stent is then cooled below its transition temperature and reshaped to a smaller-diameter coil suitable for catheter administration. After the stent in its contracted, smaller-diameter shape is delivered to the target site, e.g., via catheter, it is warmed by the body to above its transition temperature, causing the stent to assume its original expanded shape and size, typically a shape and size that anchors the stent against the walls of the vessels at the vascular site. Stents of this type are disclosed for example, in U.S. Pat. Nos. 4,512,338, 4,503,569, 4,553,545, 4,795,485, 4,820,298, 5,067,957, 5,551,954, 5,562,641, and 5,824,053. Also known in the art are graft-type stents designed for treating aneurysms, typically at relatively large-vessel sites, e.g., with vessel lumen sizes between about 15 and 30 mm. U.S. Pat. No. 4,512,338 is exemplary.

Stents such as disclosed heretofore have one or more of the following limitations, for purposes of the present invention:

(i) they are not capable of being advanced to a target site, such as a neurovascular site, that is accessible only along a tortuous path by a small-diameter catheter;
(ii) they may cause vessel injury due to rapid expansion at the target site;
(iii) they are not suitable for treating aneurysms in the absence of a special graft, sleeve or webbing;
(iv) they may cause thrombosis (clotting) of small vessels with low flow such as neurovascular vessels.

It would therefore be desirable to provide a stent that overcomes these limitations, and which is suitable, in one embodiment, for use in treating neuroaneurysms.

SUMMARY OF THE INVENTION

In one aspect, the invention includes a stent adapted for advancement through a catheter in a upstream to downstream direction to a target vessel site, in a contracted stent condition, and expulsion from the catheter, downstream end first, and radial expansion at the target site, to engage the walls of the vessel.

The stent is formed of a continuous helical ribbon, preferably formed of a shape-memory alloy, and has a bending-stiffness gradient along its length due to (i) a gradient of ribbon width, (ii) a gradient of ribbon thickness, and/or (iii) a gradient of size or number of openings formed in the stent ribbon. The stent has a preferred contracted-condition diameter of between about 10 and 30 mils, and a diameter in a fully expanded condition of between 40 and 125 mils.

In one general embodiment, the shape-memory alloy has a final austenite transition temperature of between about 25° C. and 37° C. This feature allows the stent to be moved through the catheter in a martensitic, superelastic state, and to assume its preformed, austenitic shape when expelled from the catheter. In another embodiment, the shape-memory alloy has a transition temperature $M_d$, below which the alloy retains stress-induced martensitic properties, of greater than 37° C. This allows the stent to be moved through the catheter in a stress-induced martensitic (SIM) state, and recover its preformed, austenite shape when released from the constraints of the catheter, at a temperature that may be substantially above the final austenite temperature. In this embodiment, the final austenite temperature may be quite low, e.g., 4° C., or it may be room temperature or higher.

The bending-stiffness gradient may be continuous along the length of the stent, or discontinuous, e.g., having two or more separate regions, each with substantially uniform stiffness. The stiffness gradient is typically greater stiffness upstream and lesser stiffness downstream, as the stent is oriented in the catheter for delivery in an upstream-to-downstream direction.

Where the stiffness gradient is due to a gradient of ribbon width, greater ribbon width at the upstream end of the stent, and lesser ribbon width at the downstream end of the stent, the greater ribbon width is preferably (i) at least ten times the ribbon thickness and (ii) at least two times the lesser width. The greater ribbon width is effective to reduce the rate of expansion of the stent from its contracted to its radially extended condition, relative to that of a stent having uniform winding widths equal to the lesser ribbon widths, and to increase the angle of catheter bend through which the catheter can be advanced, in an upstream to downstream direction, relative to that of a stent having uniform winding widths equal to the greater ribbon width. Preferably, the greater ribbon width is between 25 and 75 mils, and the lesser ribbon width, between 5 and 15 mils.

Where the stiffness gradient is due to a gradient of ribbon thickness, greater ribbon thickness at the upstream end of the stent, and lesser ribbon thickness at the downstream end of the stent, the greater ribbon width is preferably in the range 1–4 mils, and the greater width, between 0.5 and 2 mils. Where the stent stiffness gradient is due to fewer or smaller openings formed along the length of the helical ribbon, greater opening area in a downstream direction, the openings are preferably shaped and oriented to achieve greater stent flexibility while preserving areal coverage of the target region. In one general embodiment, the openings are I-beam shaped openings whose "I" axis is aligned transversely to the longitudinal axis of the stent in the contracted state. In another, they are Z-shaped openings whose central axis is aligned transversely to the longitudinal axis of the stent in the contracted state. The helical ribbon is effective to cover between 50% and 80% of the surface area of the vessel region containing the stent.

In a more specific embodiment, the invention includes a stent adapted for advancement through a catheter in a upstream to downstream direction to a target vessel site in a contracted stent condition, and with expulsion from the catheter, downstream end first, and radial expansion at the target site, to engage the walls of the vessel. The stent includes a continuous helical ribbon formed of a shape-memory metal having a ribbon thickness of 0.5 and 4 mils, and being effective to cover between 50% and 80% of the surface area of the vessel region containing the stent. The stent has a bending-stiffness gradient along its length due to (i) a gradient of ribbon width, (ii) a gradient of ribbon thickness; and/or a gradient of size or number of openings formed in the stent ribbon. The stent is characterized by a contracted-condition diameter of between about 10 and 30 mils, and a diameter in a fully expanded condition of between 40 and 125 mils.

In another aspect, the invention includes a catheter delivery device having a catheter for accessing an intralumenal target site, a stent of the type described above, contained within the catheter in a martensitic, superelastic state, and a catheter pusher wire for advancing the stent through the catheter in a downstream direction.

In still another aspect, the invention includes a method of treating a lesion at a neurovascular target vessel site. The method includes guiding a neuro-interventional catheter to the target site, advancing through the catheter, a stent of the type described above, and expelling the stent from the catheter at the target site, causing the stent to expand radially against the vessel walls at the target site.

The step of guiding the stent to the target site may include engaging a pusher wire releasably with the downstream end of the stent, pushing the stent through the catheter with the pusher wire, and expelling the stent from the catheter at the target site, with stent radial expansion at the target site being effective to release the stent from the pusher wire. The pusher wire can include a distal end ball adapted to be captured by the stent, with such in its contracted condition. Alternatively, the pusher wire can include a distal notch adapted to be captured by the stent, with such in its contracted condition.

These and other objects and features of the invention will become more fully apparent when the following detailed description of the invention is read in conjunction with the accompanying drawings.

DETAILED DESCRIPTION OF THE INVENTION

The present invention includes, in one aspect, a stent adapted for advancement through a catheter in a upstream to downstream direction to a target vessel site, in a contracted stent condition, and expulsion from the catheter, downstream end first, and radial expansion at the target site, to engage the walls of the vessel. The stent is formed of a continuous helical ribbon formed of a preferably shape-memory alloy, and has a bending-stiffness gradient along its length due to (i) a gradient of ribbon width, (ii) a gradient of ribbon thickness, and/or (iii) a gradient of size or number of openings formed in the stent ribbon. The stent is preferably graftless, i.e., it consists of a metal coil alone without a woven or film-like graft formed over the coil or between the coil windings, and is preferably formed of a shape-memory alloy, as discussed below.

By bending-stiffness gradient is meant a difference in bending stiffness, as measured by amount or degree of stent bending away from its long axis per force applied; that is, a region of lesser bending stiffness in the stent will exhibit greater bending in response to a given force applied in a direction normal to the stent long axis than a region of greater bending stiffness. In general, and in a preferred embodiment, the stiffness gradient is in a direction of decreasing stiffness on progressing from upstream to the downstream end of the stent, that is, from the more proximal to the more distal stent end, with the stent placed in a catheter. The stiffness gradient may be discontinuous, meaning that the gradient is formed of two or more segments of substantially uniform stiffness, or may be continuous along the length of the stent.

Figure 8:
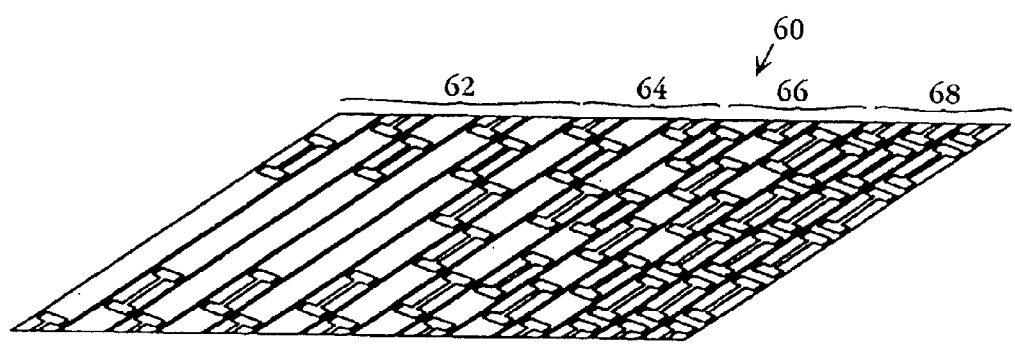
FIG. 8 is a side view of a stent constructed in accordance with a yet another general embodiment of the present invention, and shown in a contracted condition.
Figure 9:
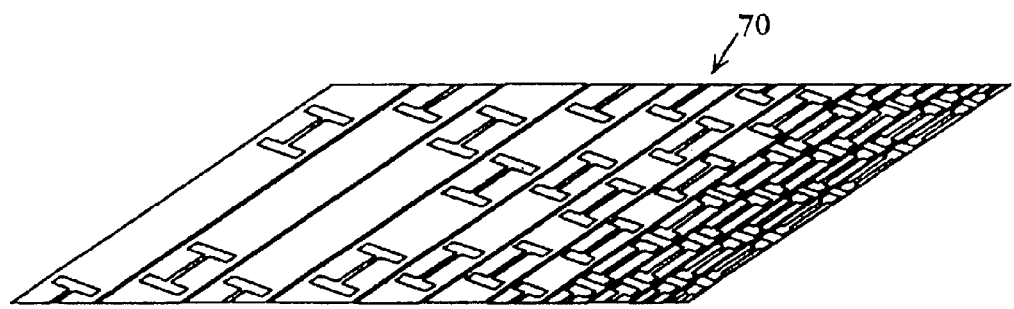
FIG. 9 is a side view of a stent constructed in accordance with another general embodiment of the present invention, and shown in a contracted condition.

Aspects of the invention will be illustrated by non-limiting embodiments having variable ribbon width (FIGS. 1–5) thickness (FIGS. 6 and 7), number of openings (FIG. 8) in the ribbon wall, or a combination of these features (FIG. 9).

Figure 1:
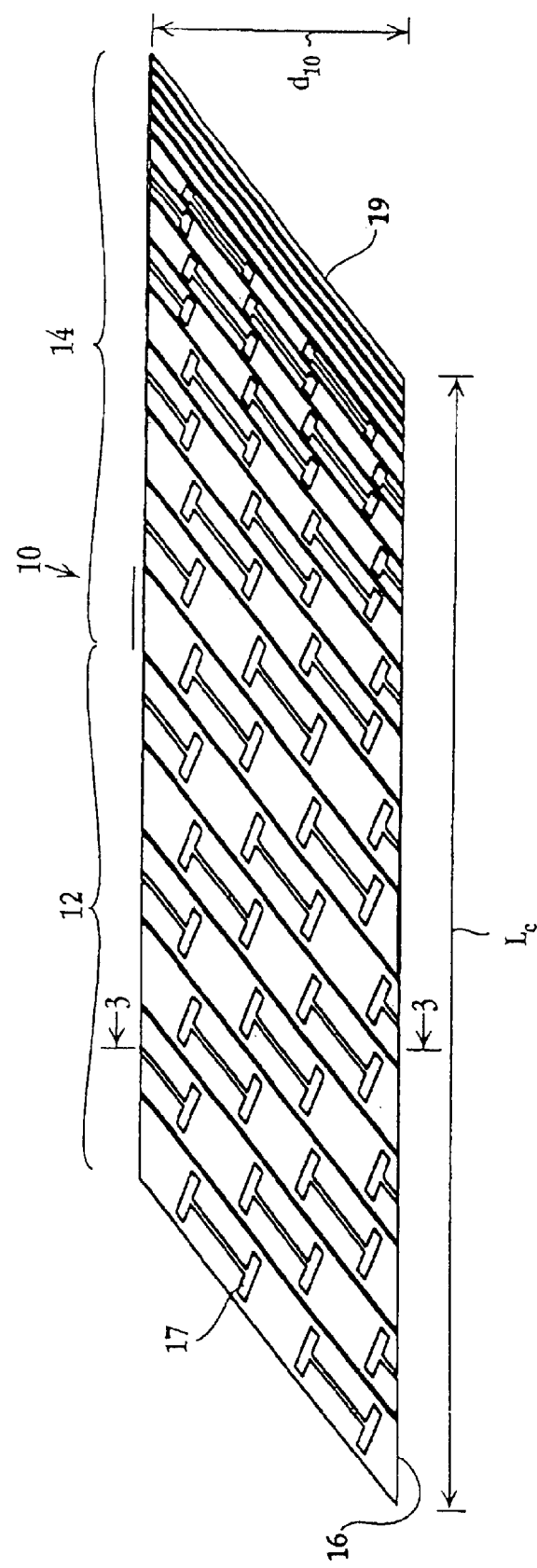
FIG. 1 is a side view of a stent constructed in accordance with one embodiment of the present invention, and shown in a contracted condition.

FIG. 1 is a side view of one embodiment of a stent 10 in accordance with the invention and is composed of a continuous helical ribbon, e.g., a coil, comprising a flat, thin and biocompatible material, such as a polymer or metal, having thermal shape memory. Stent 10 incorporates non-uniform helical winding widths in a continuous helical ribbon having an upstream portion 12 and a downstream portion 14.

In the stent 10, these portions are the same length. In other embodiments, the downstream portion can comprise from about ⅗ to ⅕ of the total length. The stent can have a gradient of ribbon widths, with greater to lesser widths progressing in an upstream-to-downstream direction. For example, the ribbon widths can be substantially uniform over the upstream half of the stent 10 shown at 12, and decrease substantially uniformly over the downstream half of the stent as shown at 14. In a typical embodiment the upstream ribbon width is about 50 mils, decreasing in increments of 10 mils at every other winding, down to about 10 mils in the downstream region of the stent. The downstream portion can comprise a region of reduced winding width which decreases substantially uniformly over the downstream half of the stent.

Preferably, the width, indicated by arrow 16, of the ribbon windings in the upstream portion is at least ten times, and more preferably at least 25 times, the ribbon thickness as indicated at 20. Preferably the ribbon width in the upstream portion is at least two times the width in the narrowest winding in the downstream portion. In stent 10, for example, the ribbon width 16 in the upstream portion 12 is at least two times the smallest ribbon width 19 in the downstream portion.

The ribbon widths in the upstream portion can be between 25 and 75 mils, and the smallest winding width in the downstream portion can be between 5 and 15 mils. In the embodiment shown (FIG. 3), the thickness 20 is constant along the length of the stent. The ribbon thickness is preferably between about 0.5 and 2 mils.

Figure 4:
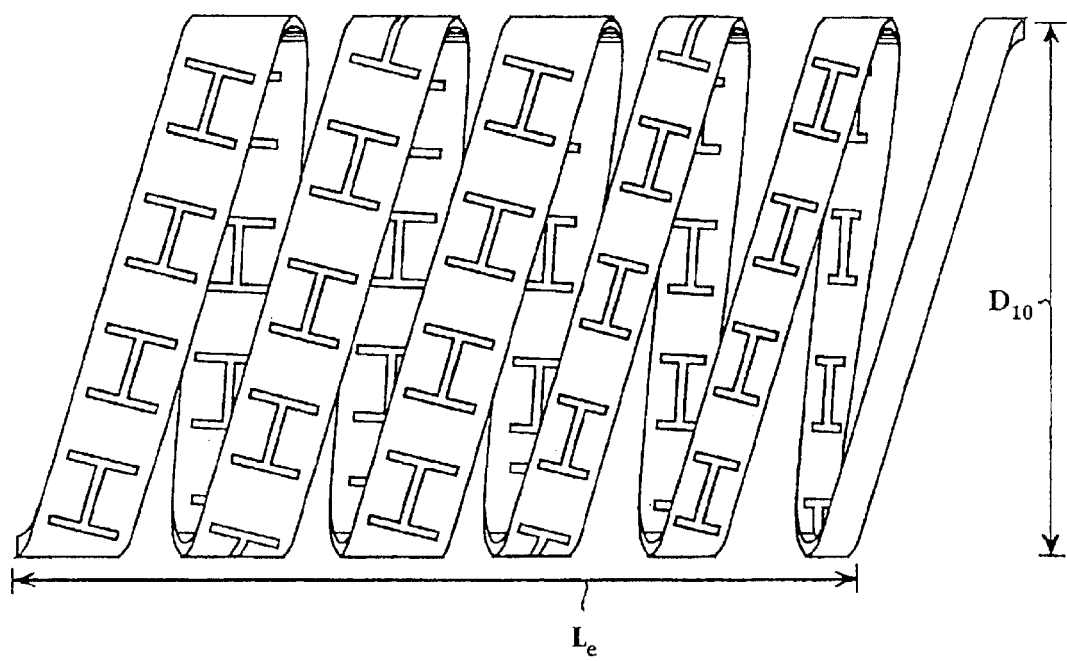
FIG. 4 is a side view of the stent in FIG. 1, but shown in an expanded 15 condition.
Figure 5:
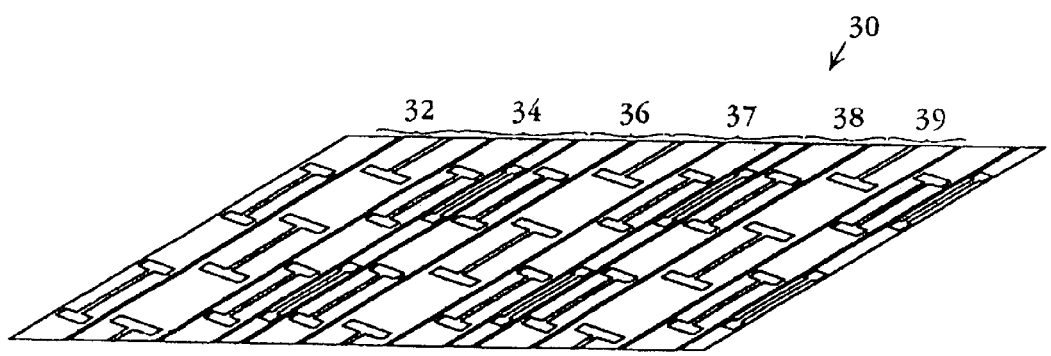
FIG. 5 is a side view of a stent constructed in accordance with another embodiment of the present invention, and shown in a contracted condition.

The ribbon is capable of existing in a contracted condition (FIG. 1) and a radially expanded condition (FIG. 4). The diameter in the contracted condition as indicated by arrow 22 can be between about 10 and 30 mils. The diameter of the fully expanded condition can be between about 40 and 125 mils.

The stent can be manufactured to have a length and diameter which are suitable for a particular therapeutic application. For example, the length in the contracted condition can be between about 50 mm to 100 mm.

In general, the ratio of the length of the stent in the contracted condition divided by the length in the expanded condition ($L_c/L_e$) will be approximately equal to the ratio of diameter of the stent in the expanded condition divided by the diameter in the contracted condition ($D_{10}/d_{10}$). Thus, a stent having a length of 50 mm and a diameter of 0.5 mm in a contracted condition will expand to a length of 10 mm and a diameter of 2.5 mm.

In another aspect of the invention, the stent can include one or more regions of lesser ribbon width intermediate the ends of the stent. For example, the stent 30 comprises non-uniform helical winding widths in a continuous helical ribbon with regions of greater and lesser ribbon widths interspersed with one another and includes regions of greater ribbon width shown at 32,36,38 and regions of lesser ribbon width shown at 34,37 and at the downstream end 39. For use in treating a lesion in a narrow and tortuous vessel, such as a neurovascular lesion, the ribbon thickness can be between 0.5 and 2 mils, the greater ribbon width can be between 25 and 75 mils, and the lesser ribbon width can be between 5 and 15 mils. Stent 30 can be manufactured by laser cutting of a nitinol hypotube, and can include openings as described hereinabove.

Figure 2A:
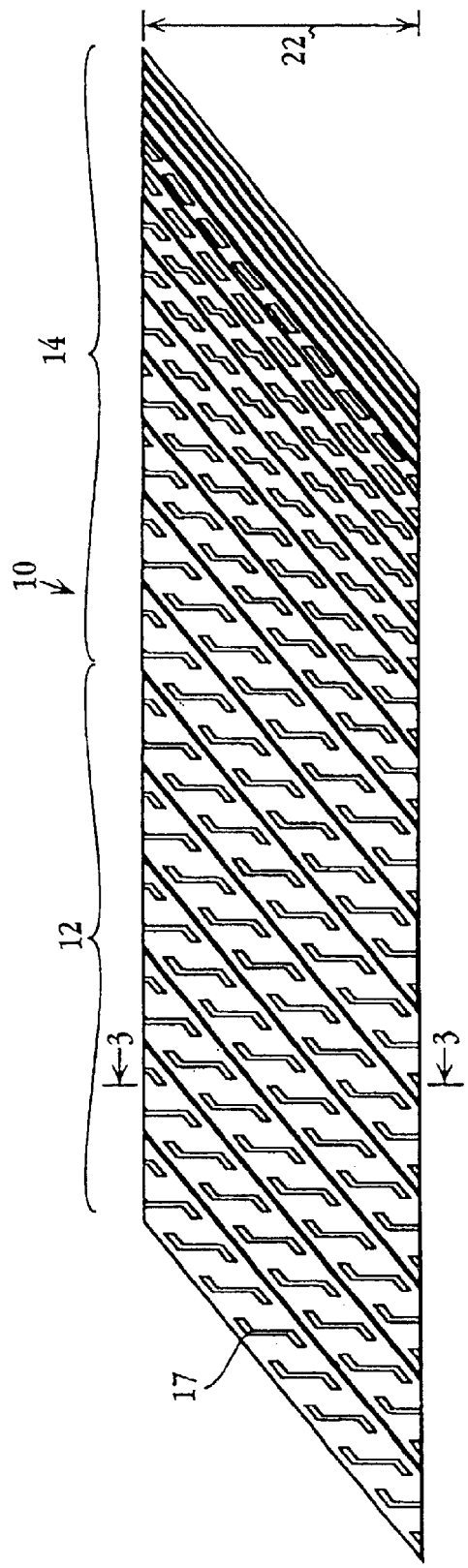
FIG. 2 is a side view (2A) of a stent constructed in another embodiment of the present invention, and shown in a contracted condition (2B)
Figure 2B:
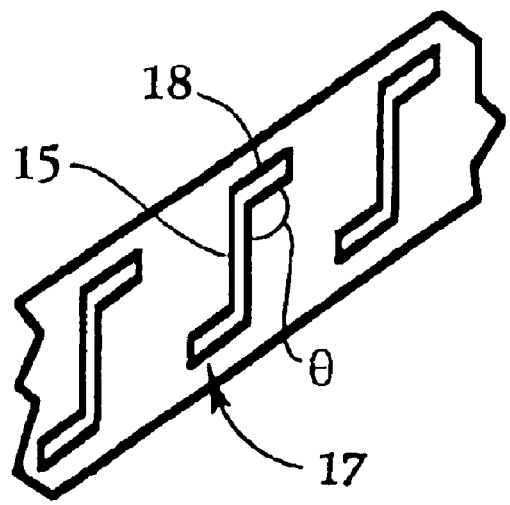
Figure 3:
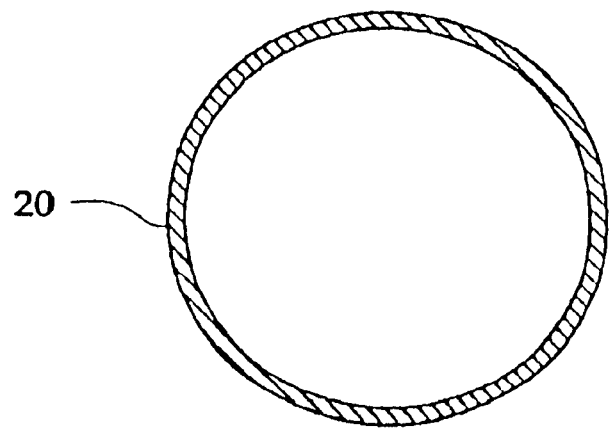
FIG. 3 is a cross-sectional view of the stent taken through line 3—3 in FIG. 1 that intersects outer surface regions of the stent.

The wall of the stent can include a plurality of openings disposed along the length of the helical ribbon. The shape of the openings can be round, oval, square, rectangular, diamond, hexagon, or polygon, and the number, size, shape of openings can be varied. A preferred opening is a crossed-beam shape such as an "X", "+", "Z", or "I" shape. Preferably, each opening has one beam axis substantially transverse to the longitudinal axis of the contracted stent. One beam can be aligned transversely to the other. An example of a shape for the opening is illustrated at 17 in FIG. 1. The openings are "I" shaped whose "I" axis is substantially transverse to the longitudinal axis of the contracted stent. Another example of a suitable opening is shown in FIG. 2A which includes a modified "Z" shaped opening. In FIG. 2B, the angle θ between an elongated central portion 15 and a terminal crossed-beam 18 is about 135° C. The openings can be formed using conventional metal working processes such as die and punch, laser cutting, or chemical etching.

In still another aspect, the stent can incorporate uniform helical winding widths in a continuous helical ribbon having portions which have different densities of openings, i.e., different numbers and or sizes of openings per unit length. The preferred shape of the openings include those described hereinabove. In an exemplary stent 60, having uniform helical winding widths (FIG. 8), the density of openings increases from the upstream toward the downstream direction as shown by reference numerals 62, 64, 66 and 68. In other embodiments, certain regions having low density of openings can be interspersed with regions having higher density of openings. In still other embodiments, certain regions can lack openings, while adjacent portions include openings. The thickness of the stent 60 is constant along the length (FIG. 8). The ribbon thickness is preferably between about 0.5 and 2 mils. The stent can be made from a shape-retaining metal alloy using the manufacturing methods described herein.

Figure 6:
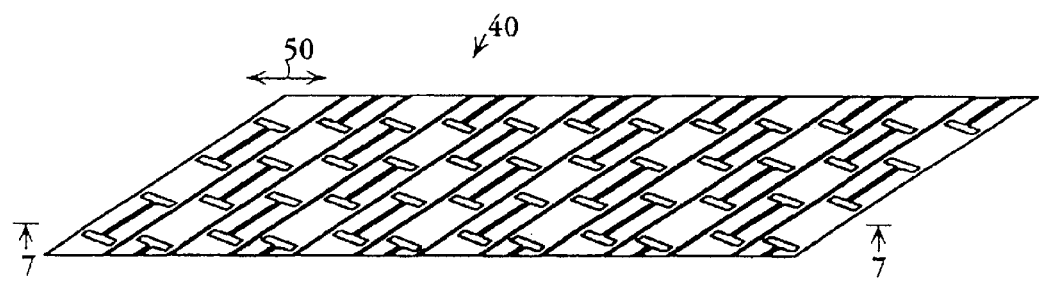
FIG. 6 is a side view of a stent constructed in accordance with a still another embodiment of the present invention, and shown in a contracted condition.
Figure 7:
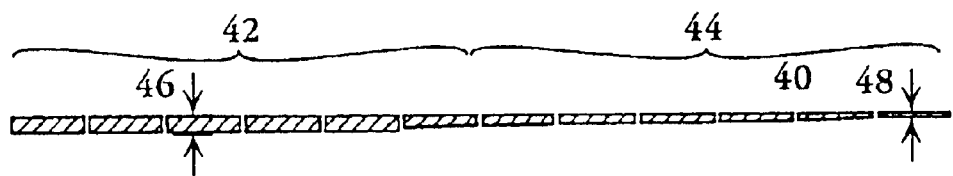
FIG. 7 is a cross-sectional view of the stent taken through line 7—7 in FIG. 6 that intersects outer surface regions of the stent.

In still another aspect, the stent can incorporate non-uniform wall thickness in a continuous helical ribbon as exemplified by stent 40 (FIGS. 6 and 7). The stent 40 has uniform winding widths, preferably between 25 and 75 mils, along the length of the ribbon. The stent includes an upstream portion 42 and a downstream portion 44, which are the same length in this embodiment. In other embodiments, the downstream portion can comprise from about ⅗ to ⅕ of the total length.

Preferably, the width as indicated by arrow 50 of the ribbon windings in the upstream portion is at least ten times, and more preferably at least 25 times, the ribbon thickness indicated by arrows 46. In a preferred embodiment, the ribbon thickness, indicated at 46, in the upstream portion is at least about two times the smallest ribbon thickness, indicated at 48, in the downstream portion. For example, the ribbon thickness in the upstream portion can be between 1 and 4 mils, and the smallest winding width in the downstream portion can be between 0.5 and 2 mils. The upstream portion can comprise a region of constant winding thickness. The downstream portion can comprise a region of reduced winding thickness which decreases substantially uniformly over the downstream half of the stent. In a typical embodiment, the upstream ribbon thickness is about 2 mil, decreasing in increments of about 0.5 mils at each winding in the downstream region to final thickness of about 0.5 mil. In an alternative embodiment, the winding thickness can decrease substantially uniformly over the whole length of the stent, from the upstream end to the downstream end. The stent 40 can include openings, and preferably crossbeam openings, as described hereinabove.

In order to form a stent having variations in wall thickness as described herein, the hypotube is subjected to centerless grinding to a wall thickness which tapers at one end, for example, having a wall thickness of 2 mil at the upstream portion 42 to about 0.5 mil at the downstream portion 44. The remaining manufacturing steps are as described herein.

In yet another aspect, the stent can incorporate along its length, combinations of more than one of the features as described herein of variable winding width, thickness, or density of openings. For example, the stent 70 (FIG. 9) includes both decreasing winding widths toward the downstream end and also an increase in density of openings toward the downstream end.

The stent preferably exhibits a relatively high degree of biocompatibility since it is implanted in the body. Suitable materials for the stent include ELGILOY (available from Carpenter Technology Corporation of Reading, Pa.) and PHYNOX (available from Metal Imphy of Imphy, France). Both of these metals are cobalt-based alloys which also include chromium, iron, nickel and molybdenum. Other materials for a self-expanding stent include 316 stainless steel and MP35N alloy which are available from Carpenter Technology Corporation and Latrobe Steel Company of Latrobe, Pa., and superelastic Nitinol nickel-titanium alloy which is available from Shape Memory Applications of Santa Clara, Calif. Nitinol alloy contains about 45% titanium.

In one general embodiment, the shape-memory alloy has a final austenite transition temperature of between about 25° C. and 37° C. This feature allows the stent to be moved through the catheter in a stress-induced martensitic or superelastic state, and assume its preformed, austenitic shape when expelled from the catheter by removing the stress imposed on the stent by the inner catheter wall and causing the now unstressed stent to transform from stress-induced martensite into austenite and thus regaining its austenitic shape. In another embodiment, the shape-memory alloy has a transition temperature $M_d$ greater than 37° C. below which the alloy retains sufficient stress-induced martensitic property to allow placement of the stent at or above its $A_f$. In other words, this allows the stent to be moved through the catheter in a stress-induced martensitic (SIM) state, and recover its preformed, austenitic shape when released from the constraints of the catheter, at a temperature that may be substantially above the final austenite temperature without significant plastic, or otherwise permanent deformation. In this embodiment, the final austenite temperature may be quite low, e.g., 4° C., or it may be room temperature of higher.

Nitinol cylindrical tubes having a final austenitic temperature between about 25° C. and 45° C., preferably about 25° C. and 37° C., can be prepared according to known methods. In an exemplary method of manufacture of the stent having these properties, a nitinol hypotube, e.g., 8 mil wall thickness, is subjected to centerless grinding to a wall thickness of 3 mil. The stent pattern is cut by a laser (e.g., as described by Madou in Fundamentals of Microfabrication, CRC Press, 1997). Both inner and outer surfaces are polished to a mirror finish using electro-polish techniques (e.g., as described by Madou, 1997). A gold coat is applied by ion beam assist.

During manufacture, the ribbon is formed at the expanded condition (FIG. 4), corresponding to the final deployed size (e.g., about 2–4 mm outer diameter), and heated to a temperature above the transition temperature. The ribbon is then subjected to thermoelastic martensitic transformation (e.g., as described in U.S. Pat. No. 5,190,546 incorporated by reference in its entirety herein) by cooling below the transition temperature range of the alloy and deformation to the contracted condition suitable for use within an intraluminal catheter. For example, the stent can be rolled using a rod having a notch at one end which engages the downstream end of the stent. The transition temperature can be modified by varying the ratios of each metal in the alloy and in the present invention preferably is within the range between about 25° C. to 45° C. at which the stent expands. A more preferred transition temperature range is between about 25° C. to 37° C. For example, the alloy can comprise 55% nickel, and 45% titanium which gives a transition temperature of about 32° C. to 33° C., which is below body temperature but above room temperature.

Nitinol cylindrical tubes having a martensite temperature $M_D$ below which the alloy can assume a stress-induced martensitic condition while being stressed to the extent necessary to place or otherwise use the device, of greater than about 37° C., preferably greater than about 40° C., are also prepared according to known methods, e.g., U.S. Pat. No. 4,505,767. For example an ideal alloy would act, at about 37° C., as a constant force spring over a strain range up to about 5% or more. This is a measurement of the degree to which an alloy, at a given temperature, can be strained in a purely austenitic state by the formation of stress-induced martensite without significant plastic deformation. In other words, the strain caused by the application of a given stress at a given temperature is substantially recoverable. In practice, the maximum stress realized occurs sometime during the process of placing a nitinol device at a given temperature. Accordingly, a suitable alloy will provide a device that is capable of substantially recovering its austenitic shape without significant plastic deformation, upon placement in the body.

The operation of the stent of the invention will now be discussed in reference to device 10 for the sake of clarity, and not by way of limitation, it being appreciated that any other embodiment can be used in the same manner.

Figure 10A:
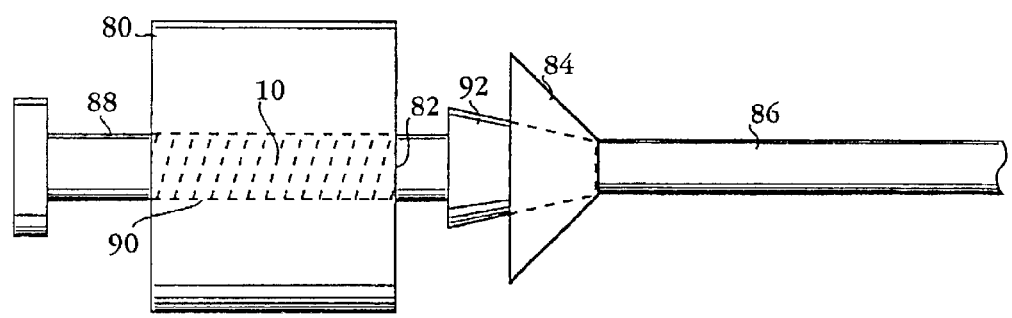
FIGS. 10A–10C illustrate one embodiment of a method for loading the 30 stent of the invention into the proximal end of a catheter.
Figure 10B:
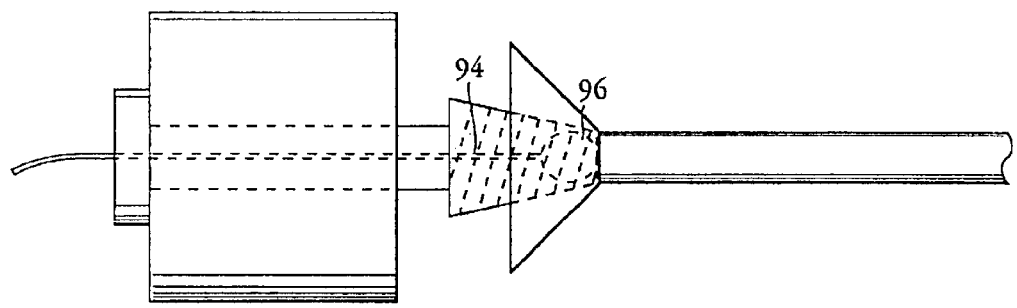
Figure 10C:
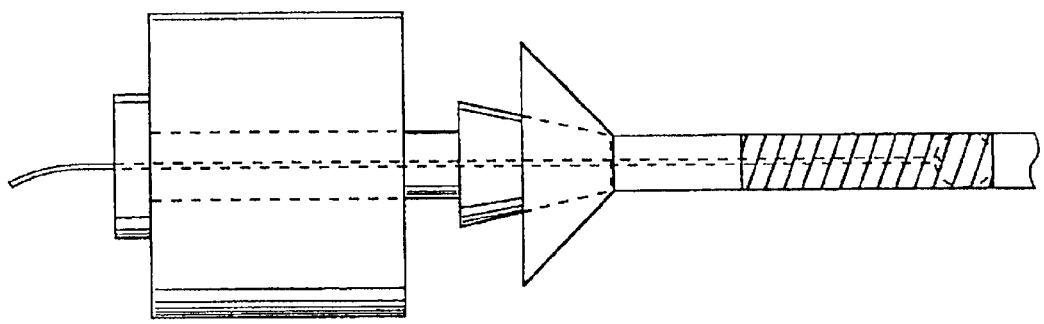

The helical stent is loaded into a catheter as illustrated in FIGS. 10A–10C. The catheter and loaded stent form a device in accordance with another aspect of the invention. The device may additionally include a pusher wire for advancing the stent through the lumen of the catheter, as described below.

Prior to loading, the stent can be retained in a contracted condition, e.g. within a cartridge 80. The stent can be wrapped around a mandrel (not represented) prior to placement within the cartridge. The downstream end of the stent is loaded into hub 84 of a delivery system such as a catheter 86. Depression of plunger 88 pushes the stent from its holding chamber 90 into the distal end 92 of the cartridge. A pusher wire 94 is then introduced into the hub of the catheter. The inner wall of the downstream end of the stent frictionally engages end ball 96 mounted to the distal end of the pusher wire 94. The pusher wire is then pushed downstream through the catheter in order to advance the stent, in a contracted condition, to the target site. Thus, the stent is dragged through the catheter by the end ball near the tip which drags the stent near (but not at) its downstream end.

Figure 11A:
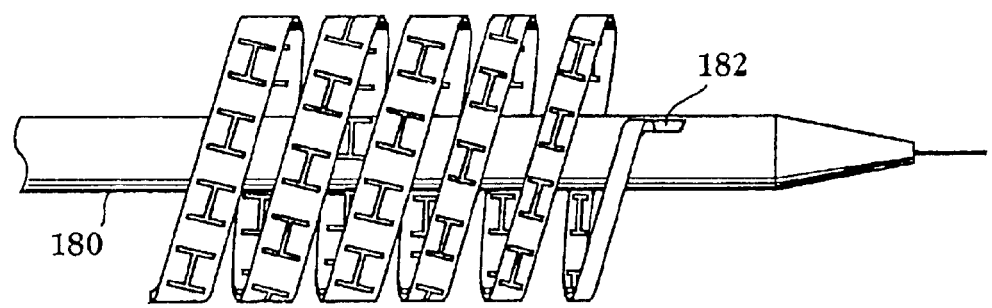
FIGS. 11A–11C illustrate another embodiment of a method for loading the stent of the invention into the proximal end of a catheter.
Figure 11B:
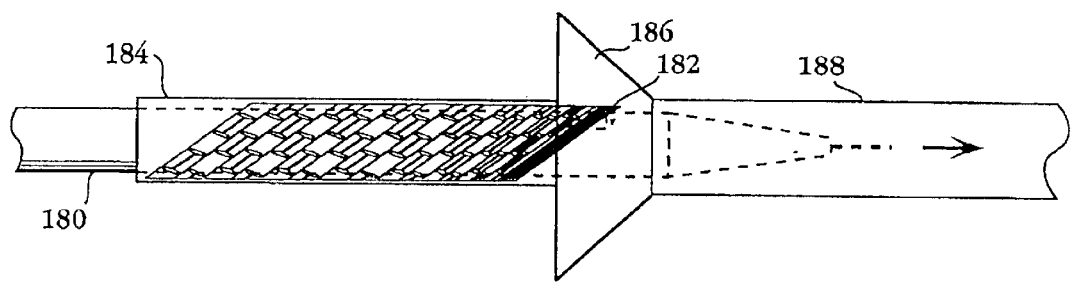
Figure 11C:
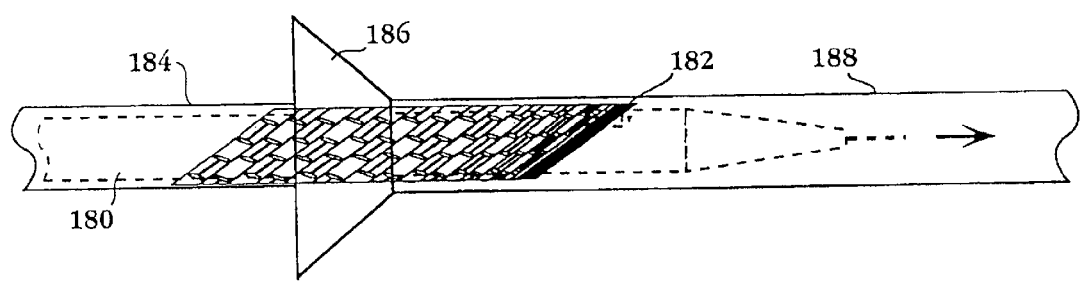

Another method for loading the stent into a catheter uses a pusher wire 180 having a distal notch 182 adapted to hold the downstream end of the stent as illustrated in FIGS. 11A–11C. The wire can have more than one notch along its length for attachment to more than one location on the stent (not illustrated). With the stent at a temperature below the transition temperature, the pusher wire 180 is rotated along its longitudinal axis to wind the stent to its contracted condition. The stent is manually inserted into and retained within a retaining sleeve 184. An example of a suitable sleeve is a 15–20 cm section of polymeric microcatheter (Target Therapeutics, Freemont, Calif.). The sleeve is positioned at the opening of the hub 186 of catheter 188 and the stent is advanced in its contracted state from the sleeve and into the catheter (as indicated by arrow 190) using the pusher wire.

Figure 12A:
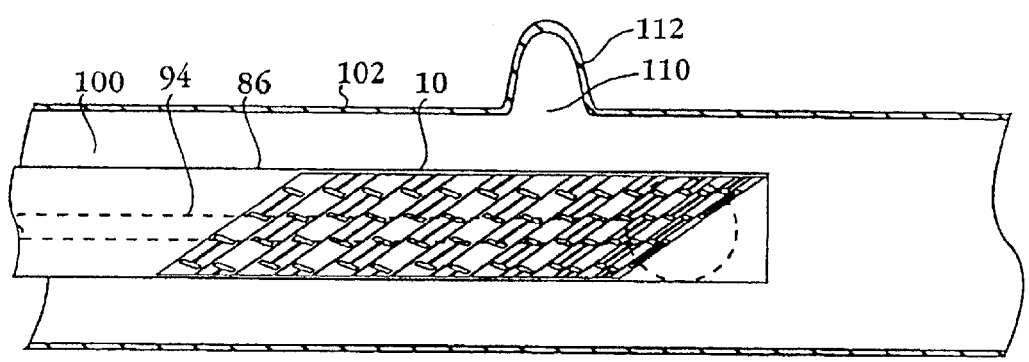
FIGS. 12A–12D illustrate steps in the use of the stent treating a neuroaneurysm, in accordance with the method of the invention.

In another aspect of the invention, the stent is used in the treatment of a variety of vascular lesions. This aspect will be illustrated in FIGS. 12A–12D using stent 10 of the invention in a method for treating a neurovascular aneurysm. In accordance with the method, a catheter 86 is guided within the lumen 100 of a vessel 102 to the lesion site using fluoroscopy and standard angiographic techniques (FIG. 12A). Preferably the pusher wire 94 is held steady and the catheter is retracted in an upstream direction, as indicated by arrow 106 to partially release the stent 10 downstream end first (FIG. 12B).

During release from the catheter, the stent is "naked" and free-moving; that is, it is not mounted on a balloon, constrained by a sheath, or held in place by a tethering wire. The stent does not deploy while partially outside of the catheter (FIG. 12B) and can be repositioned or removed as desired.

Figure 12B:
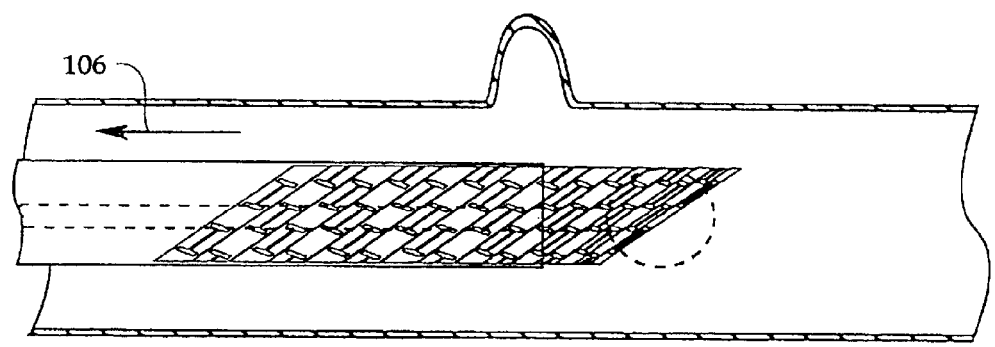
Figure 12C:
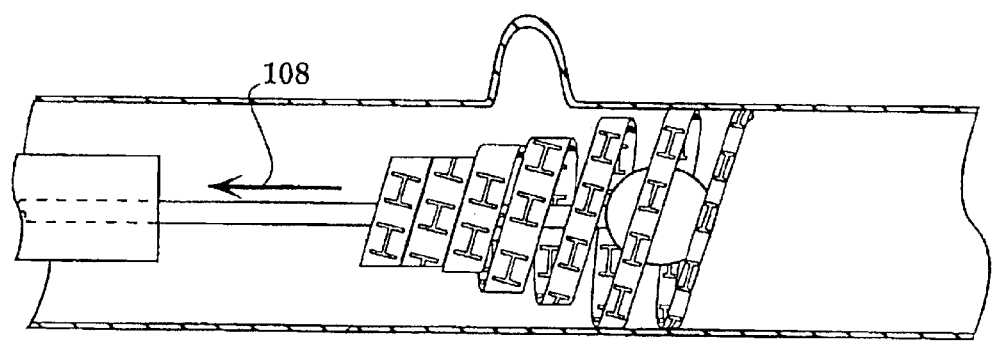
Figure 12D:
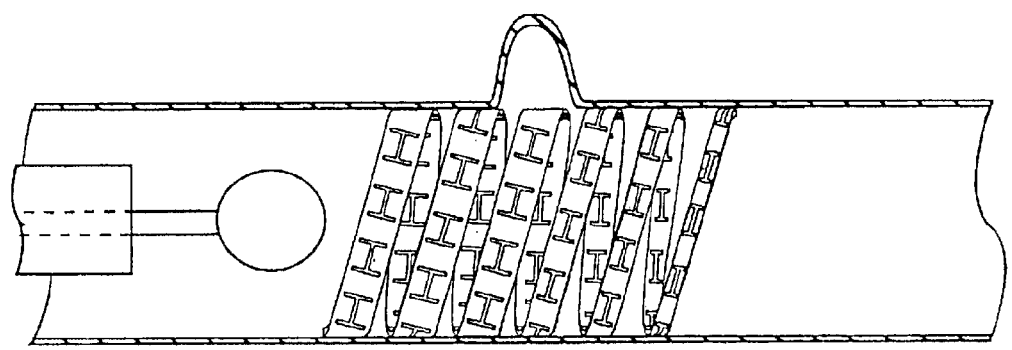

During the final stage of deployment, the pusher wire is held steady, and the catheter is retracted, as shown by arrow 106, to fully expel the stent (FIG. 12B). Warming of the stent to body temperature at the target site causes the stent to expand radially against the vessel walls at the target site. The expansion causes release of the end ball, allowing withdrawal of the pusher wire, as shown by arrow 108 (FIGS. 12C, 12D) to complete the procedure. The stent deploys once it is completely outside the catheter (FIG. 12D).

When using a pusher wire having a terminal notch, the pusher wire is pushed downstream through the catheter in order to advance the stent, in a contracted condition, to the target site. The stent disengages the notch upon deployment at the target site (not shown).

When used in the treatment of an aneurysm, for example, a high percentage of surface area coverage is needed to effectively cover the mouth 110 of the aneurysm 112 (FIG. 12A). A preferred helical ribbon of the invention is effective to cover between 50% and 80%, and preferably between 65% and 80%, of the surface area of the vessel region containing the fully expanded stent. The length of the stent is selected so that in the expanded state, it extends beyond both sides of the mouth of the aneurysm.

The stent of the present invention can be used in the treatment of a variety of vascular lesions such as an aneurysm, fistula, occlusion, or narrowing and is useful in treating targets located in tortuous and narrow vessels, for example in the neurovascular system, or in certain sites within the coronary vascular system, or in sites within the peripheral vascular system such as superficial femoral, popliteal, or renal arteries.

As described herein, the stent incorporates longitudinal gradients of structural features to achieve the flexibility, rate of radial expansion from a contracted to an expanded state, coverage of void space, and radial strength which are desired for its intended use. For example, as described herein, the ribbon width can be selected during manufacture. In a particular example, stent 10 is substantially cylindrical in both its contracted and expanded conditions. However, during the initial stages of deployment, the greater ribbon width along the upstream portion of the stent promotes slower expansion after the stent is released form the catheter, relative to the expansion of a stent having uniform winding widths equal to a smallest winding width in the downstream portion. The slower expansion advantageously reduces the risk of trauma to the vessel wall. The greater ribbon width gives more surface coverage of the vessel wall and also provides more uniform apposition against the wall which lowers hemodynamic turbulence and lowers the risk of vascular thrombosis.

In general, narrower winding widths confer increased flexibility. Stent 10 incorporates downstream portions having relatively lesser ribbon widths. As compared to a stent having uniform ribbon widths equal to the largest winding width in the upstream portion, the lesser ribbon widths provide a decrease in stiffness to the stent which increases the angle of bend through which the stent can be advanced in a contracted condition. This is especially important for advancing the stent within a catheter positioned within a tortuous vessel. Higher flexibility also allows the stent to conform to vessel curvature at the target site. Stent 30 includes intermediate portions having lesser winding widths, which also increase the flexibility of the stent.

Likewise, the ribbon thickness can be varied as in stent 40, with greater thickness generally slower rate of expansion above the transition temperature, and greater radial strength, as compared to thinner ribbon windings. Thinner winding widths generally confer increased flexibility. Stent 40 incorporates downstream portions having relatively lesser ribbon thickness. As compared to a stent having uniform ribbon thickness equal to the largest winding width in the upstream portion, the lesser ribbon thickness provides a decrease in stiffness to the stent which increases the angle of bend through which the stent can be advanced in a contracted condition. This is especially important for advancing the stent within a catheter positioned within a tortuous blood vessel. Higher flexibility also allows the stent to conform to vessel curvature at the target site. It will be recognized that a stent can include intermediate portions having lesser winding thickness, in analogy with stent 30, which can also increase the flexibility of the stent.

As described herein, the ribbon wall of the stent can incorporate openings. The shape, orientation, and size of the openings can be selected during manufacture. The density of openings can influence the radial strength of the stent, the rate of expansion, the flexibility and the area of surface coverage. Different portions of a stent can have different density of openings, or different sizes and shapes of openings, as shown in FIGS. 7 and 8. Greater density of openings in ribbon windings generally gives greater flexibility.

Stent 60, for example, incorporates downstream portions having relatively greater density of openings. As compared to a stent having uniform density of openings along the ribbon equal to the lowest density of openings in the upstream portion, the higher density of openings provides a decrease in stiffness to the stent which increases the angle of bend through which the stent can be advanced in a contracted condition. This is especially important for advancing the stent within a catheter positioned within a tortuous vessel. A stent can include intermediate portions having regions of higher or lower density of openings which can also increase the flexibility of the stent.

Applicant has determined that a shape which incorporates a "crossed-beam" opening disposed along the length of the helical ribbon, where each opening has at least one beam axis substantially transverse to the longitudinal axis of the stent, has the advantage of facilitating the bending of a stent, in the contracted condition, in both a direction longitudinal to the axis of the stent and in a direction transverse to the longitudinal axis of the stent. For a stent in the expanded condition, such openings minimize the size of the opening, to give greater surface coverage, while maximizing the radial strength of the stent. An example of a preferred opening is an I-beam shaped opening having the "I" axis transverse to the longitudinal axis of the stent in the contracted condition. Another example is a "Z" shaped opening where the central portion of the "Z" is linearly extended and is transverse to the longitudinal axis of the stent in the contracted state.

The size and shape of the openings can be varied to increase or decrease the contact area between the stent and the vessel wall. The openings and the spacing between adjacent ribbon windings contribute to void space which is needed to promote efficient endothelial-cell growth on and around the stent. A void space of about 15% to 50% is preferred.

It will be appreciated that the present invention provides a stent having a variety of features which can be varied during the manufacturing process in order to optimize the structure of the stent for its intended use. More than one feature, such as width, thickness, or shape or density of openings can be combined, to achieve desired flexibility, rate of expansion, or area of surface coverage. For example, stent 70 incorporates variations in both helical windings widths and density of openings.

In the process of manufacture, the stent of the invention preferably includes thin wall construction which contributes to greater lumen diameter in the stent region, and minimizes blood flow turbulence at the upstream edge of the stent, thereby reducing the risk of blood clotting.

The stent preferably is manufactured to minimize adverse effects, such as thrombosis, which can occur during use such as a result of hemodynamic turbulence, internal hyperplasia, and reaction to a foreign body. For example, the manufacturing processes includes an electro-polishing step to give the stent a mirror finish a gold coating step to improve biocompatibility.

A variety of other modifications can also be made. For example, the stent can be coated to enhance radiopacity, such as by using gold or another radiopaque metal. It can be coated with drugs or chemical agents to promote faster and more complete clotting of the aneurysm sac, to minimize the thromobogenicity of the stent in the artery, and to provide other functions. It can be covered with an autologous or synthetic graft, or coated to fill the void areas of the stent.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A catheter-stent device for treating an intravascular lesion at a target site of a vessel, comprising
   (a) a catheter having proximal and distal ends, and an inner lumen extending therebetween, said catheter being guidable to place the distal catheter end at the target site, and
   (b) a stent, the stent having a length, an upstream end and a downstream end, adapted for advancement through the catheter in an upstream to downstream direction to the target site in a contracted stent condition, and with expulsion from the catheter, downstream end first, and radial expansion at the target site, to engage the wall of the vessel, the entirety of the stent forming a single conduit,
   said stent being formed of a continuous helical ribbon having a ribbon thickness effective to cover between 50% and 80% of a vessel region containing the length of the stent and having a bending-stiffness gradient along its length due to one or more of the following:
      (i) a gradient of ribbon width, greater ribbon width at the upstream end of the stent, and lesser ribbon width at the downstream end of the stent, and
      (ii) a gradient of size or number of openings formed in the continuous helical ribbon, greater opening area progressing in a downstream direction.

2. The device of claim 1, which further includes a pusher wire for advancing the stent through the catheter in the upstream to the downstream direction, wherein the pusher wire engages the stent, pushing the stent through the catheter and expelling the stent from the catheter at the target site, the stent radial expansion at the target site being effective to release the stent from the pusher wire.

3. The device of claim 2, wherein the pusher wire has an expanded portion which engages the stent.

4. The device of claim 2, wherein the downstream end of the stent is connected to a notch on the end of the pusher wire.

5. The device of claim 2, wherein the pusher wire engages the downstream end of the stent without engaging the upstream end of the stent.

6. The device of claim 2, wherein the stent is releasably attached to the pusher wire, for release therefrom, when the stent is released and expands to its expanded condition.

7. The device of claim 1, wherein the continuous helical ribbon is a shape-memory alloy having a final austenite transition temperature about 25° C. and 37° C.

8. The device of claim 1, wherein the continuous helical ribbon is a shape-memory alloy having a transition temperature $M_d$ below which the alloy retains stress-inducted martensitic properties of greater than 37° C.

9. The device or claim 1, wherein the stent has a contracted-condition diameter of between about 10 and 30 mils, and a diameter in a fully expanded condition of between 40 and 125 mils.

10. The device of claim 1, wherein the bending-stiffness gradient in the stent is due to the gradient of ribbon width, where the greater ribbon width is (i) at least ten times the ribbon thickness and (ii) at least two times the lesser width, said greater ribbon width being effective to reduce the rate of expansion of the stent from its contracted to its radially extended condition, relative to that of a stent having uniform winding widths equal to the lesser ribbon width, said lesser ribbon width being effective to increase an angle of catheter bend through which the catheter can be advanced, in the upstream to downstream direction, relative to that of a stent having uniform winding widths equal to the greater ribbon width.

11. The device of claim 10, wherein the stent ribbon thickness is between 0.5 and 2 mils, the greater ribbon width is between 25 and 75 mils, and the lesser ribbon width is between 5 and 15 mils.

12. The device of claim 1, wherein the bending-stiffness gradient is further due to a gradient of ribbon thickness.

13. The device of claim 1, wherein the bending-stiffness gradient is due to fewer or smaller openings formed along the length of the helical ribbon.

14. The stent of claim 1, wherein the openings are I-beam shaped openings whose "I" axis is aligned transversely to the longitudinal axis of the stent in the contracted condition, or Z-shaped openings whose central axis is aligned transversely to the longitudinal axis of the stent in the contracted condition.

15. The device of claim 1, the stent having a non-zero pitch along its length.

16. The device of claim 1, wherein the ribbon, when stretched out, is straight.

17. The device of claim 1, wherein the stent is constructed and arranged such that it does not deploy until it is free from the catheter.

18. The device of claim 1, wherein target site is a neurovascular aneurysm.

19. The device of claim 1, wherein the bending-stiffness gradient is a decreasing stiffness from the upstream end of the stent to the downstream end of the stent.

20. A catheter-stent device for treating an intravascular lesion at a target site of a vessel, comprising (a) a catheter having proximal and distal ends, and an inner lumen extending therebetween, said catheter being guidable to place the distal catheter end at the target site, and (b) a stent, the stent being a ribbon having a thickness, adapted for advancement through the catheter in an upstream to downstream direction to the target site in a contracted stent condition, and with expulsion from the catheter, downstream end first, and radial expansion at the target site, to engage the wall of the vessel, the entirety of the stent forming a single conduit, said stent having a bending-stiffness gradient along its length due to a gradient of ribbon width, a greater ribbon width at the upstream end of the stent, and a lesser ribbon width at the downstream end of the stent, where the greater ribbon width is (i) at least ten times the ribbon thickness and (ii) at least two times the lesser ribbon width, said greater ribbon width being effective to reduce the rate of expansion of the stent from its contracted to its radially expanded condition, relative to that of a stent having uniform winding widths equal to the lesser ribbon widths, said lesser ribbon width being effective to increase an angle of catheter bend through which the catheter can be advanced, in the upstream to downstream direction, relative to that of a stent having uniform winding widths equal to the greater ribbon width.

21. The device of claim 20, wherein the ribbon thickness is between 0.5 and 2 mils, the greater ribbon width is between 25 and 75 mils, and the lesser ribbon width is between 5 and 15 mils.

* * * * *